United States Patent [19]

Findeisen et al.

[11] Patent Number: 5,021,081
[45] Date of Patent: Jun. 4, 1991

[54] HERBICIDAL SUBSTITUTED TRIAZOLES

[75] Inventors: Kurt Findeisen, Odenthal; Markus Lindig, Hilden; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 324,361

[22] Filed: Mar. 15, 1989

[30] Foreign Application Priority Data

Mar. 18, 1988 [DE] Fed. Rep. of Germany ....... 3809053

[51] Int. Cl.$^5$ .................. A01N 43/653; C07D 249/14
[52] U.S. Cl. ..................................... 71/92; 548/264.8; 548/265.6
[58] Field of Search ................. 548/266, 264.8, 265.6; 71/92

[56] References Cited

U.S. PATENT DOCUMENTS 2,670,282  3/1952  Allen ....................................... 71/92

FOREIGN PATENT DOCUMENTS 1695377  4/1971  Fed. Rep. of Germany .
0242612  2/1987  Fed. Rep. of Germany .
0242616  2/1987  Fed. Rep. of Germany .
0919458  2/1963  United Kingdom .

OTHER PUBLICATIONS

Chemical Abstracts, vol. 85, No. 11, Sep. 13, 1976, p. 487.

Primary Examiner—Robert W. Ramsuer
Assistant Examiner—Patricia L. Morris
Attorney, Agent, or Firm—Sprung Horn Kramer & Woods

[57] ABSTRACT

Herbicidal substituted triazoles of the formula

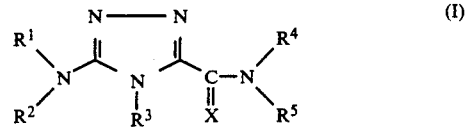

in which

R$^1$ and R$^2$ independently of one another each stands for hydrogen, alkyl, alkenyl, alkinyl, halogenoalkyl, halogenoalkenyl, halogenoalkinyl, alkoxyalkyl, cycloalkyl, cycloalkylalkyl, for in each case optionally substituted aryl, aralkyl or heteroaryl, or together with the nitrogen atom to which they are bonded stand for an optionally substituted heterocyclic ring, R$^3$ stands for alkyl, alkenyl, alkinyl, halogenoalkyl, halogenoalkenyl, halogenoalkinyl, alkoxyalkyl, cycloalkylalkyl, cycloalkyl or for in each case optionally substituted aralkyl or aryl, R$^4$ and R$^5$ independently of one another each stands for hydrogen, alkyl, alkenyl, alkinyl, halogenoalkyl, halogenoalkenyl, halogenoalkinyl, cyanoalkyl, hydroxyalkyl, alkoxyalkyl, alkylaminoalkyl, dialkylaminoalkyl, alkoximinoalkyl, alkoxycarbonylalkyl, alkoxycarbonylalkenyl, for in each case optionally substituted cycloalkyl, cycloalkylalkyl, cycloalkenyl or cycloalkenylalkyl, for in each case optionally substituted heterocyclylalkyl, for in each each case optionally substituted aralkyl, aroyl or aryl, or together with the nitrogen atom to which they are bonded stand for an optionally substituted heterocyclic ring, and X stands for oxygen or sulphur.

9 Claims, No Drawings

HERBICIDAL SUBSTITUTED TRIAZOLES

The invention relates to new substituted triazoles, several processes for their preparation and their use as herbicides.

It is known that certain nitrogen-containing heterocyclic compounds, such as, for example, N-isobutyl-imidazolidin-2-one-1-carboxamide (cf., for example, K.H. Büchel "Pflanzenschutz und Schädlingsbekämpfung" [Plant Protection and Pest Control] p. 170, Thieme Verlag Stuttgart 1977) possess herbicidal properties.

However, the herbicidal activity of these previously known compounds against problem weeds and their tolerance by important crop plants is not completely satisfactory in all fields of application.

New substituted triazoles of the general formula (I)

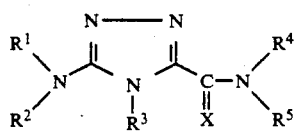

in which
$R^1$ and $R^2$ independently of one another each stand for hydrogen, alkyl, alkenyl, alkinyl, halogenoalkyl, halogenoalkenyl, halogenoalkinyl, alkoxyalkyl, cycloalkyl, cycloalkylalkyl, for in each case optionally substituted aryl, aralkyl or heteroaryl, or together with the nitrogen atom to which they are bonded stand for an optionally substituted heterocyclic ring,
$R^3$ stands for alkyl, alkenyl, alkinyl, halogenoalkyl, halogenoalkenyl, halogenoalkinyl, alkoxyalkyl, cycloalkylalkyl, cycloalkyl or for in each case optionally substituted aralkyl or aryl,
Rhu 4 and $R^5$ independently of one another each stand for hydrogen, alkyl, alkenyl, alkinyl, halogenoalkyl, halogenoalkenyl, halogenoalkinyl, cyanoalkyl, hydroxyalkyl, alkoxyalkyl, alkylaminoalkyl, dialkylaminoalkyl, alkoximinoalkyl, alkoxycarbonylalkyl, alkoxycarbonylalkenyl, for in each case optionally substituted cycloalkyl, cycloalkylalkyl, cycloalkenyl or cycloalkenylalkyl, for in each case optionally substituted heterocyclylalkyl, for in each case optionally substituted aralkyl, aroyl or aryl, or together with the nitrogen atom to which they are bonded stand for an optionally substituted heterocyclic ring, and
X stands for oxygen or sulphur,
have been found.

Furthermore, it has been found that the new substituted triazoles of the general formula (I)

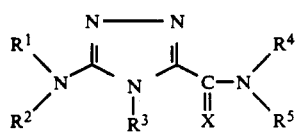

in which
$R^1$ and $R^2$ independently of one another each stand for hydrogen, alkyl, alkenyl, alkinyl, halogenoalkyl, halogenoalkenyl, halogenoalkinyl, alkoxyalkyl, cycloalkyl, cycloalkylalkyl, for in each case optionally substituted aryl, aralkyl or heteroaryl, or together with the nitrogen atom to which they are bonded stand for an optionally substituted heterocyclic ring,
$R^3$ stands for alkyl, alkenyl, alkinyl, halogenoalkyl, halogenoalkenyl, halogenoalkinyl, alkoxyalkyl, cycloalkylalkyl, cycloalkyl or for in each case optionally substituted aralkyl or aryl,
$R^4$ and $R^5$ independently of one another each stand for hydrogen, alkyl, alkenyl, alkinyl, halogenoalkyl, halogenoalkenyl, halogenoalkinyl, cyanoalkyl, hydroxyalkyl, alkoxyalkyl, alkylaminoalkyl, dialkylaminoalkyl, alkoximinoalkyl, alkoxycarbonylalkyl, alkoxycarbonylalkenyl, for in each case optionally substituted cycloalkyl, cycloalkylalkyl, cycloalkenyl or cycloalkenylalkyl, for in each case optionally substituted heterocyclylalkyl, for in each case optionally substituted aralkyl, aroyl or aryl, or together with the nitrogen atom to which they are bonded stand for an optionally substituted heterocyclic ring, and
X stands for oxygen or sulphur,
are obtained in a process in which
(a) aminoguanidines of the formula (II)

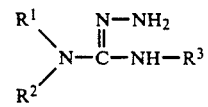

in which
$R^1$, $R^2$ and $R^3$ have the abovementioned meaning,
or their acid addition salts are reacted with (thio)oxalic ester amides of the formula (III)

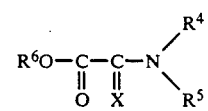

in which
$R^6$ stands for alkyl and
$R^4$, $R^5$ and X have the abovementioned meaning, if appropriate in the presence of a diluent and if appropriate in the presence of a reaction auxiliary, or in which
(b) substituted triazolyl(thio)carboxylic acid esters of the formula (IV)

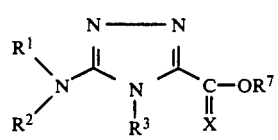

in which
$R^7$ stands for alkyl and
$R^1$, $R^2R^3$ and X have the abovementioned meaning, are reacted with amines of the formula (V)

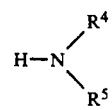

in which
$R^4$ and $R^5$ have the abovementioned meaning, if appropriate in the presence of a diluent.

Finally, it has been found that the new substituted triazoles of the general formula (I) possess herbicidal properties.

Surprisingly, the substituted triazoles of the general formula (I) according to the invention show a considerably better herbicidal effectiveness towards problem weeds than the nitrogen-containing heterocyclic compounds which are known from the prior art, such as, for example, N-isobutylimidazolidin-2-one-1-carboxamide.

Formula (I) provides a general definition of the substituted triazoles according to the invention. Preferred compounds of formula (I) are those in which $R^1$ and $R^2$ independently of one another each stand for hydrogen, for in each case straight-chain or branched alkyl which has 1 to 8 carbon atoms, alkenyl which has 2 to 8 carbon atoms, alkinyl which has 2 to 8 carbon atoms, halogenoalkyl which has 1 to 8 carbon atoms and 1 to 17 identical or different halogen atoms, halogenoalkenyl or halogenoalkinyl, each of which has 2 to 8 carbon atoms and 1 to 15 or 13 identical or different halogen atoms respectively, alkoxyalkyl which has 1 to 6 carbon atoms in the individual alkyl moieties, for cycloalkyl which has 3 to 7 carbon atoms, for cycloalkylalkyl which has 3 to 7 carbon atoms in the cycloalkyl moiety and 1 to 6 carbon atoms in the straight-chain or branched alkyl moiety or for aralkyl which has 6 to 10 carbon atoms in the aryl moiety and 1 to 6 carbon atoms in the straight-chain or branched alkyl moiety, for aryl which has 6 to 10 carbon atoms or for heteroaryl which has 2 to 9 carbon atoms and 1 to 3 hetero atoms, in particular nitrogen, oxygen and/or sulphur, each of which is optionally substituted once or more than once by identical or different substituents from the series comprising halogen, cyano, nitro and also in each case straight-chain or branched alkyl, alkoxy, alkylthio, halogenoalkyl, halogenoalkoxy or halogenoalkylthio, each of which has 1 to 4 carbon atoms and if appropriate 1 to 9 identical or different halogen atoms, or $R^1$ and $R^2$ together with the nitrogen atom to which they are bonded stand for a five- to ten-membered heterocyclic ring which may contain, if appropriate, 1 to 2 other hetero atoms, in particular nitrogen, oxygen and/or sulphur, and which is optionally substituted once or more than once by identical or different substituents, suitable substituents being: halogen and also in each case straight-chain or branched alkyl or halogenoalkyl, each of which has 1 to 4 carbon atoms and if appropriate 1 to 9 identical or different halogen atoms and also 1 to 2 oxo or thiono groups, $R^3$ stands for in each case straight-chain or branched alkyl which has 1 to 8 carbon atoms, alkenyl which has 2 to 8 carbon atoms, alkinyl which has 2 to 8 carbon atoms, halogenoalkyl which has 1 to 8 carbon atoms and 1 to 17 identical or different halogen atoms, halogenoalkenyl which has 2 to 8 carbon atoms and 1 to 15 identical or different halogen atoms, halogenoalkinyl which has 2 to 8 carbon atoms and 1 to 13 identical or different halogen atoms, alkoxyalkyl which has 1 to 6 carbon atoms in each of the individual alkyl moieties, for cycloalkylalkyl or cycloalkyl each of which has 3 to 7 carbon atoms in the cycloalkyl moiety and if appropriate 1 to 6 carbon atoms in the straight-chain or branched alkyl moiety, or for aralkyl or aryl, each of which has 6 to 10 carbon atoms in the aryl moiety and if appropriate 1 to 6 carbon atoms in the straight-chain or branched alkyl moiety and each of which is optionally substituted once or more than once by identical or different substituents, suitable aryl substituents in each case being: halogen, cyano, nitro and also in each case straight-chain or branched alkyl, alkoxy, alkylthio, halogenoalkyl, halogenoalkoxy or halogenoalkylthio, each of which has 1 to 4 carbon atoms and if appropriate 1 to 9 identical or different halogen atoms, $R^4$ and $R^5$ independently of one another each stand for hydrogen, for in each case straight-chain or branched alkyl which has 1 to 18 carbon atoms, alkenyl which has 2 to 8 carbon atoms, alkinyl which has 2 to 8 carbon atoms, halogenoalkyl which has 1 to 8 carbon atoms and 1 to 17 identical or different halogen atoms, halogenoalkenyl or halogenoalkinyl, each of which has 2 to 8 carbon atoms and 1 to 15, or 13, identical or different halogen atoms, respectively, cyanoalkyl which has 1 to 8 carbon atoms, hydroxyalkyl which has 1 to 8 carbon atoms and 1 to 6 hydroxyl groups, alkoxyalkyl, alkoximinoalkyl, alkoxycarbonylalkyl or alkoxycarbonylalkenyl, each of which has up to 6 carbon atoms in the individual alkyl moieties, or alkenyl moities, respectively, alkylaminoalkyl or dialkylaminoalkyl, each of which has 1 to 6 carbon atoms in the individual alkyl moieties, or for cycloalkyl, cycloalkylalkyl, cycloalkenyl or cycloalkenylalkyl, each of which has 3 to 8 carbon atoms in the cycloalkyl moiety, or cycloalkenyl moiety, respectively, and if appropriate 1 to 6 carbon atoms in the straight-chain or branched alkyl moiety and each of which is optionally substituted once or more than once by identical or different substituents from the series comprising halogen, cyano and in each case straight-chain or branched alkyl or halogenoalkyl, each of which has 1 to 4 carbon atoms and if appropriate 1 to 9 identical or different halogen atoms or in each case double-linked alkanediyl, or alkenediyl, each of which has up to 4 carbon atoms; furthermore for heterocyclylalkyl which has 1 to 6 carbon atoms in the straight-chain or branched alkyl moiety and 1 to 9 carbon atoms and also 1 to 3 hetero atoms—in particular nitrogen, oxygen and/or sulphur—in the heterocyclyl moiety and which is optionally substituted once or more than once in the heterocyclyl moiety by identical or different substitents, suitable substituents being: halogen, cyano, nitro, and also in each case straight-chain or branched alkyl, alkoxy, alkylthio, halogenoalkyl, halogenoalkoxy, halogenoalkylthio or alkoxycarbonyl, each of which has 1 to 5 carbon atoms and if appropriate 1 to 9 identical or different halogen atoms, and, in addition, for aralkyl, aroyl or aryl, each of which has 6 to 10 carbon atoms in the aryl moiety and if appropriate 1 to 8 carbon atoms in the straight-chain or branched alkyl moiety and each of which is optionally substituted once or more than once by identical or different substituents, suitable aryl substituents in each case being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl, each of which has 1 to 6 carbon atoms and if appropriate 1 to 9 identical or different halogen atoms, cycloalkyl which has 3 to 6 carbon atoms or phenoxy, and suitable alkyl substituents, if appropriate, being: halogen or cyano, or $R^4$ and $R^5$ together with the nitrogen atom to which they are bonded stand for a five- to ten-membered heterocyclic ring which may contain, if appropriate, 1 to 2 more hetero atoms, in particular nitrogen, oxygen and/or sulphur, and which is optionally substituted once or more than once by identical or different substituents, suitable substituents being: halogen and also in each case straight-chain or branched alkyl or halogenoalkyl, each of which has 1 to 4 carbon atoms and if appropriate 1 to 9 identical or different halogen atoms and also 1 or 2 oxo or thiono groups, and X stands for oxygen or sulphur.

Particularly preferred compounds of the formula (I) are those in which $R^1$ and $R^2$ independently of one another each stand for hydrogen, for methyl, ethyl, n- or i-propyl, n-, i-, s- or t-butyl, n- or i-pentyl, allyl, propargyl, for in each case straight-chain or branched halogenoalkyl which has 1 to 4 carbon atoms, halogenoalkenyl which has 3 to 6 carbon atoms or halogenoalkinyl which has 3 to 6 carbon atoms, each of which has 1 to 9 identical or different halogen atoms, for methoxymethyl, methoxyethyl, for cyclopropyl, cyclopropylmethyl, cyclopentyl, cyclohexyl, cyclohexylmethyl, cyclohexylethyl, cyclopentylmethyl or for benzyl, phenylethyl or phenyl, each of which is optionally substituted once to three times by indentical or different substituents, suitable substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, or $R^1$ and $R^2$ together with the nitrogen atom to which they are bonded stand for a heterocyclic ring of the formula

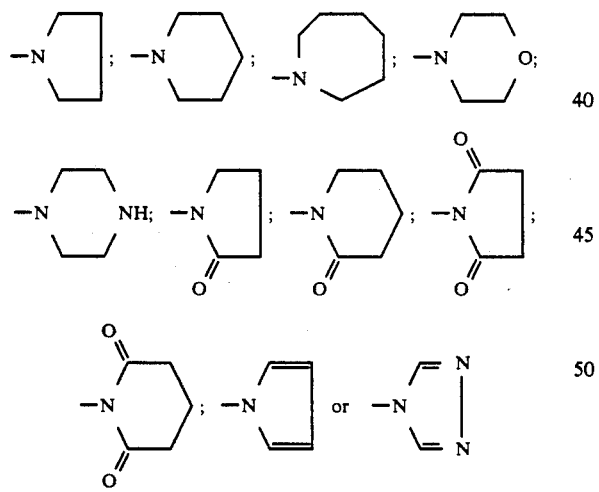

each of which is optionally substituted once to three times by identical or different substituents, suitable substituents in each case being: methyl, ethyl, n- or i-propyl, chlorine or trifluoromethyl, $R^3$ stands for methyl, ethyl, n- or i-propyl, n-, i-, s- or t-butyl, n- or i-pentyl, n- or i-hexyl, for allyl, propargyl, for methoxymethyl, for straight-chain or branched halogenoalkyl which has 1 to 4 carbon atoms and 1 to 9 identical or different halogen atoms, in particular, fluorine, chlorine or bromine, for cyclopentyl, cyclohexyl, cyclopropyl, cyclopropylmethyl, cyclohexylmethyl, cyclohexylethyl or for benzyl or phenyl, each of which is optionally substituted once to three times by identical or different substituents, suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, $R^4$ and $R^5$ independently of one another each stand for hydrogen, methyl, ethyl, n- or i-propyl, n, i, s- or t-butyl, in each case straight-chain or branched, in particular n or iso, pentyl, hexyl, heplyl, octyl, nonyl, decyl or dodecyl, for allyl, n- or i-butenyl, n-or i-pentenyl, n- or i-hexenyl, propargyl, n- or i-butinyl, n- or i-pentinyl, n- or i-hexinyl, for straight-chain or branched halogenoalkyl which has 1 to 6 carbon atoms and 1 to 9 identical or different halogen atoms, in particular fluorine, chlorine or bromine, for in each case straight-chain or branched halogenoalkenyl or halogenoalkinyl each of which has 3 to 5 carbon atoms and 1 to 3 halogen atoms, in particular fluorine or chlorine, for in each case straight-chain or branched cyanoalkyl which has 1 to 6 carbon atoms in the alkyl moiety, hydroxyalkyl which has 1 to 6 carbon atoms and 1 to 3 hydroxyl groups, alkoxyalkyl, alkoximinoalkyl, alkoxycarbonylalkyl or alkoxycarbonylalkenyl, alkylaminoalkyl or dialkylaminoalkyl, each of which has up to 4 carbon atoms in the individual alkyl moieties, or alkenyl moieties, respectively, or for cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is optionally substituted once to three times by identical or different substituents, suitable substituents in each case being: fluorine, chlorine, bromine, methyl, ethyl, n- or i-propyl, n-, i-, s- or t-butyl, cyano, methanediyl, ethanediyl, butanediyl or butadienediyl; additionally stand for heterocyclylmethyl, heterocyclylpropyl or heterocyclylethyl, each of which is optionally substituted once to three times in the heterocyclyl moiety by identical or different substituents, suitable heterocyclic rings in each case being:

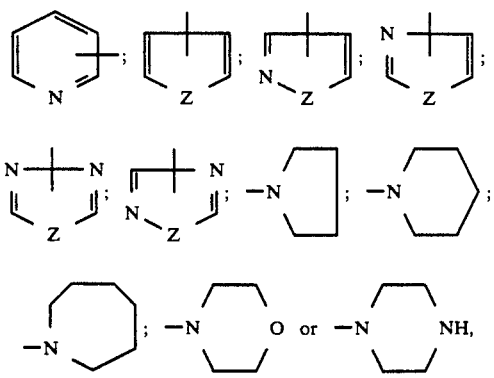

where Z in each case stands for oxygen or sulphur, and suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio; additionally stands for optionally straight-chain or branched benzyl, phenylethyl, phenylpropyl, phenylbutyl, phenylpentyl, phenylhexyl, phenylheptyl, phenylcyanomethyl, phenylcyanoethyl, phenylcyanopropyl, benzoyl, phenyl or naphthyl, each of which is optionally substituted once to three times by identical or different substituents, suitable phenyl substituents in each case being: fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trilfuoromethylsulphinyl, trifluoromethylsulphonyl, methyl sulphinyl, methylsulphonyl, acetyl, propionyl, methoxycarbonyl, ethoxycarbonyl, cyclohexyl or phenoxy, or $R^4$ and $R^5$ together with the nitrogen atom to which they are bonded stand for a heterocyclic ring of the formula

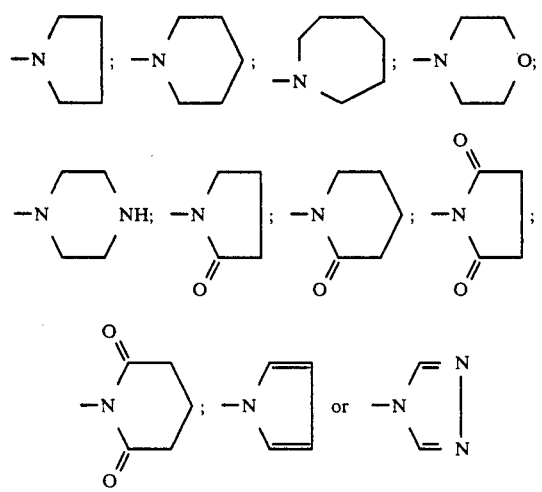

each of which is optionally substituted once to three times by identical or different substituents, suitable substituents in each case being: methyl, ethyl, n- or i-propyl, chlorine or trifluoromethyl, and X stands for oxygen or sulphur.

Very particularly preferred compounds of the formula (I) are those in which $R^1$ stands for hydrogen, methyl or ethyl, $R^2$ stands for methyl or ethyl, $R^3$ stands for methyl or ethyl, $R^4$ stands for hydrogen or methyl, $R^5$ stands for hydrogen, methyl, ethyl, n- or i-propyl, n-, i-, s- or t-butyl, in each case straight chain or branched, in particular n or iso, pentyl, hexyl, heptyl, octyl, nanyl, decly or dodecyl, for allyl, n- or i-butenyl, n- or i-pentenyl, n- or i-hexenyl, propargyl, n- or i-butinyl, n- or i-pentinyl, n- or i-hexinyl, for straight-chain or branched halogenoalkyl which has 1 to 6 carbon atoms and 1 to 9 identical or different halogen atoms, in particular fluorine, chlorine or bromine, for in each case straight-chain or branched halogenoalkenyl or halogenoalkinyl, each of which has 3 to 5 carbon atoms and 1 to 3 halogen atoms, in particular fluorine or chlorine, for in each case straight-chain or branched cyanoalkyl which has 1 to 6 carbon atoms in the alkyl moiety, hydroxyalkyl which has 1 to 6 carbon atoms and 1 to 3 hydroxyl groups, alkoxyalkyl, alkoximinoalkyl, alkoxycarbonylalkyl or alkoxycarbonylalkenyl, alkylaminoalkyl or dialkylaminoalkyl, each of which has up to 4 carbon atoms in the individual alkyl moieties, or alkenyl moieties, respectively, or for cyclopropyl, cyclopropylmethyl, cyclopropylethyl, cyclobutyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is optionally substituted once to three times by identical or different substituents from the series comprising fluorine, chlorine, bromine, methyl, ethyl, n- or i-propyl, n-, i-, s- or t-butyl, cyano, methanediyl, ethanediyl, butanediyl or butadienediyl; additionally stands for heterocyclylmethyl, heterocyclylpropyl or heterocyclylethyl, each of which is optionally substituted once to three times in the heterocyclyl moiety by identical or different substituents from the series comprising fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, suitable heterocyclic rings in each case being:

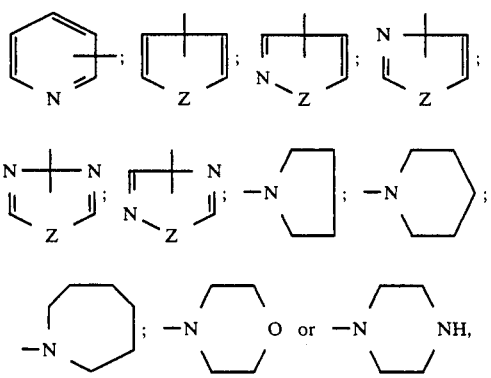

with Z in each case standing for oxygen or sulphur, additionally stands for in each case straight-chain or branched benzyl, phenylethyl, phenylpropyl, phenylbutyl, phenylpentyl, phenylhexyl, phenylheptyl, phenylcyanomethyl, phenylcyanoethyl, phenylcyanopropyl, benzoyl, phenyl or naphthyl, each of which is optionally substituted once to three times in the phenyl moiety by identical or different substituents from the series comprising fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulfinyl, trifluoromethylsulphonyl, methylsulphinyl, methylsulphonyl, acetyl, propionyl, methoxycarbonyl, ethoxycarbonyl, cyclohexyl or phenoxy, and X stands for oxygen.

In particular preferred compounds of the formula (I) are those in which $R^1$ stands for methyl or ethyl, $R^2$ stands for methyl or ethyl, $R^3$ stands for methyl or ethyl, $R^4$ stands for hydrogen or methyl, $R^5$ stands for hydrogen, methyl, ethyl, n- or i-propyl, n-, i-, s- or t-butyl, in each case straight-chain or branched, in particular n or iso, pentyl, hexyl, heptyl, octyl, nonyl, decyl or dodecyl, for allyl, n- or i-butenyl, n- or i-pentenyl, n- or i-hexenyl, propargyl, n- or i-butinyl, n- or i-pentinyl, n- or i-hexinyl, for straight-chain or branched halogenoalkyl which has 1 to 6 carbon atoms and 1 to 9 identical or different halogen atoms, in particular fluorine, chlorine or bromine, for in each case straight-chain or branched halogenoalkenyl or halogenoalkinyl, each of which has 3 to 5 carbon atoms and 1 lo 3 halogen atoms, in particular fluorine or chlorine, for in each case straight-chain or branched cyanoalkyl which has 1 to 6 carbon atoms in the alkyl moiety, hydroxyalkyl which has 1 to 6 carbon atoms and 1 to 3 hydroxyl groups or alkoxyalkyl which has 1 to 4 carbon atoms in the individual alkyl parts, or for cyclopropyl, cyclopropylmethyl, cyclopropylethyl, cyclobutyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is optionally substituted once to three times by identical or different substituents from the series comprising fluorine, chlorine, bromine, methyl, ethyl, n- or i-propyl, n-, i-, s- or t-butyl, cyano; additionally stands for pyridylmethyl which is optionally substituted once to three times in the heterocyclyl moiety by identical or different substituents from the series comprising fluorine, chlorine, bromine, cyano, nitro, methyl, ethyl, n-or i-propyl, n-, i-, s- or t-butyl, methoxy, ethoxy, methylthio, trifluoromethyl, trifluoromethoxy or trifluoromethylthio, additionally stands for in each case straight-chain or branched benzyl, phenylethyl, phenylpropyl, phenylbutyl, phenylpentyl, phenylhexyl, phenylheptyl, each of which is optionally substituted once to three times in the phenyl moiety by identical or different substituents from the series comprising fluorine, chlorine, bromine, hydroxyl, cyano, nitro, methyl, ethyl, n-or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, and X stands for oxygen.

The following substituted triazoles of the general formula (i) may be mentioned individually in additional to the compounds mentioned in the Preparation Examples:

$$\begin{array}{c} N\text{———}N \\ R^1\diagdown \qquad \diagup R^4 \\ N=\qquad =C-N \\ R^2\diagup \quad N \quad X \quad \diagdown R^5 \\ \quad\quad R^3 \end{array} \quad (I)$$

| R¹ | R² | R³ | R⁴ | R⁵ | X |
|---|---|---|---|---|---|
| CH₃ | CH₃ | C₂H₅ | H | —C(CH₃)₃ | O |
| H | CH₃ | CH₃ | H | cyclohexyl-H | O |
| H | CH₃ | C₂H₅ | H | —CH₂—C(CH₃)₃ | O |
| H | CH₃ | C₂H₅ | H | —CH(CH₃)—phenyl | O |
| CH₃ | CH₃ | CH₃ | CH₃ | —C(CH₃)₃ | O |
| CH₃ | CH₃ | C₂H₅ | CH₃ | —C(CH₃)₃ | O |
| C₂H₅ | C₂H₅ | CH₃ | H | —C(CH₃)₂—CF₃ | O |
| H | C₂H₅ | CH₃ | H | —C(CH₃)₃ | O |
| H | CH₃ | CH₃ | CH₃ | —C(CH₃)₃ | O |
| CH₃ | CH₃ | CH₃ | H | —CH(CH₃)—CH=N—OCH₃ | O |
| CH₃ | CH₃ | CH₃ | CH₃ | —CH(CH₃)—CH=N—OCH₃ | O |
| H | CH₃ | CH₃ | H | —CH(CH₃)—CH=N—OCH₃ | O |

If, for example, 1-amino-2,2,3-trimethylguanidinium hydrochloride and monoethyl oxalate N-allylamide are used as starting substances, the course of the reaction of process (a) according to the invention may be represented by the following equation:

$$\begin{array}{c} CH_3\diagdown \quad N-NH_2 \\ \quad\quad \| \\ N-C-NH-CH_3 \times HCl \;+ \\ CH_3\diagup \end{array}$$

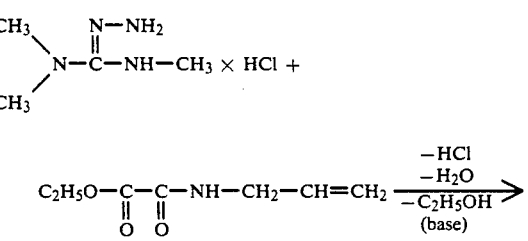

$$\begin{array}{c} N\text{———}N \\ CH_3-N=\quad =C-NH-CH_2-CH=CH_2 \\ \quad\quad\; N \quad\quad \| \\ CH_3 \quad CH_3 \quad O \end{array}$$

If, for example, ethyl 5-dimethylamino-4-methyl-4H-1,2,4-triazol-3-yl-carboxylate and benzylamine are used as starting substances, the course of the reaction of process (b) according to the invention may be represented by the following equation:

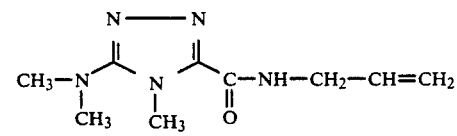

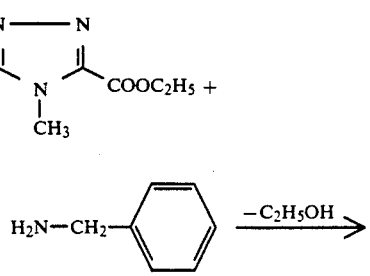

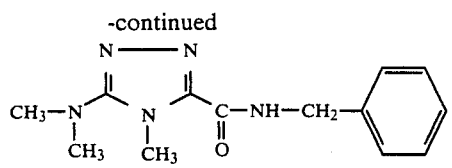

Formula (II) provides a general definition of the aminoguanidines required as starting substances for carrying out process (a) according to the invention. In this formula (II), $R^1$, $R^2$ and $R^3$ preferably stand for those radicals which have already been mentioned in connection with the description of the substances of the formula (I) according to the invention as being preferred for these substituents.

The aminoguanidines of the formula (II) or their acid addition salts, such as, in particular, their hydrochlorides or hydrobromides, are known or can be obtained in analogy to known processes, for example in a process in which the generally known ureas of the formula (VI)

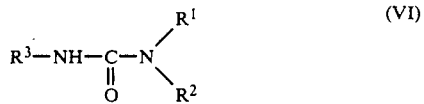

in which
$R^1$, $R^2$ and $R^3$ have the abovementioned meaning, are initially reacted, in a first step, with phosgene at temperatures between $+10°$ C. and $+150°$ C., if appropriate in the presence of a diluent such as, for example, toluene or acetonitrile, and the resulting formamidine hydrochlorides of the formula (VII)

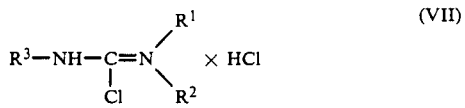

in which
$R^1$, $R^2$ and $R^3$ have the abovementioned meaning, are reacted, in a second step, with hydrazine hydrate at temperatures between $-10°$ C. and $+60°$ C., if appropriate in the presence of a diluent, such as, for example, isopropanol or dichloromethane (cf., for example, J. org. Chem. 19, 1807 [1954]; Bull. Soc. Chim. Fr. 1975, 1649; U.S. Pat. No. 2,845,458).

Ureas of the formula (VI) are generally known compounds of organic chemistry.

Formula (III) provides a general definition of the (thio)oxalic ester amides furthermore required as starting substances for carrying out process (a) according to the invention. In this formula (III), $R^4$, $R^5$ and X preferably stand for those radicals which have already been mentioned in connection with the description of the substances of the formula (I) according to the invention as being preferred for these substituents.

$R^6$ preferably stands for straight-chain or branched alkyl which has 1 to 4 carbon atoms, in particular for methyl or ethyl.

The (thio)oxalic ester amides of the formula (III) are generally known or can be obtained in analogy to generally known processes (cf., for example, Houben-Weyl, "Methoden der organischen Chemie" [Methods of Organic Chemistry], Volume VIII, p. 659, Thieme Verlag Stuttgart; U.S. Pat. No. 2,857,390; Compt. rend. Acad. Sci. 230, 848 [1950]; GB 1,578,719; DE-OS (German Published Specification) 2,819,878; DE-OS (German Published Specification) 1,227,451).

Formula (IV) provides a general definition of the triazolyl(thio)carboxylic acid esters required as starting substances for carrying out process (b) according to the invention. In this formula (IV), $R^1$, $R^2$, $R^3$ and X preferably stand for those radicals which have already been mentioned in connection with the description of the substances of the formula (I) according to the invention as being preferred for these substituents.

$R^7$ preferably stands for straight-chain or branched alkyl which has 1 to 4 carbon atoms, in particular for methyl or ethyl.

Some of the triazolyl(thio)carboxylic acid esters of the formula (IV) are known or can be obtained in analogy to known processes (cf., for example, EP 48,555; EP 16,565; EP 150,507; Ref. Zh., Khim 1984, Abstr. No. 3 ZH 271 or C.A. 101: 54 999e) for example when aminoguanidines of the formula (II)

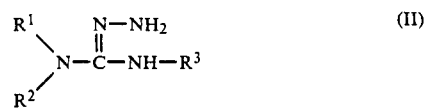

in which
$R^1$, $R^2$ and $R^3$ have the abovementioned meaning, or their acid addition salts, such as, in particular, their hydrochlorides, are reacted with (thio)oxalic acid esters of the formula (VIII)

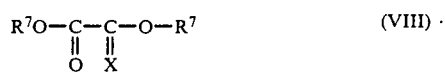

in which
$R^7$ and X have the abovementioned meaning, at temperatures from $70°$ C. to $250°$ C., if appropriate in the presence of a diluent, such as, for example, acetonitrile or 1,2-dichlorobenzene.

(Thio)oxalic acid esters of the formula (VIII) are generally known or can be obtained in analogy to known processes (cf., for example, Liebigs Ann. Chem. 1974, 671-689 or Tetrahedron 33, 259-263 [1977]).

Formula (V) provides a general definition of the amines required as starting substances for carrying out process (b) according to the invention. In this formula (V), $R^4$ and $R^5$ preferably stand for those radicals which have already been mentioned in connection with the description of the substances of the formula (I) according to the invention as being preferred for these substituents.

The amines of the formula (V) are generally-known compounds of organic chemistry.

Suitable diluents for carrying out process (a) are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran, ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or alcohols, such as methanol, ethanol or propanol.

If appropriate, process (a) according to the invention is carried out in the presence of a suitable reaction auxiliary. Suitable reaction auxiliaries are all inorganic and organic bases which can customarily be used. The hydrides, hydroxides, amides, alkoxides, carbonates or hydrogen carbonates of alkali metals, such as, for example, sodium hydride, sodium amide, sodium hydroxide, sodium methoxide, sodium ethoxide, potassium t-butoxide, sodium carbonate or sodium hydrogen carbonate, or also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably used.

When carrying out process (a) according to the invention, the reaction temperatures can be varied within a relatively wide range. In general, the process is carried out at temperatures from 30° C. to 150° C., preferably at temperatures from 50° C. to 80° C.

For carrying out process (a) according to the invention, 1.0 to 1.5 moles, preferably 1.0 to 1.2 moles, of (thio)oxalic ester amide of the formula (III) and if appropriate 1.0 to 5.0 moles, preferably 1.0 to 2.5 moles, of reaction auxiliary are employed per mole of aminoguanidine of the formula (II) or of a corresponding acid addition salt. The reaction is carried out, and the reaction products are worked up and isolated by generally customary methods (cf. also the Preparation Examples).

Suitable diluents for carrying out process (b) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran, ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide.

When carrying out process (b) according to the invention, the reaction temperatures can be varied within a relatively wide range. In general, the process is carried out at temperatures from 50° C. to 250° C., preferably at temperatures from 100° C. to 220° C.

If appropriate, process (b) can also be carried out under pressure. The process is preferably carried out in pressure ranges from 1.0 to 50.0 bar, in particular in pressure ranges from 3.0 to 20.0 bar.

For carrying out process (b) according to the invention, 1.0 to 1.5 moles, preferably 1.0 to 1.2 moles, of amine of the formula (V) are generally employed per mole of substituted triazolyl(thio)carboxylic acid ester of the formula (IV).

The reaction is carried out, and the reaction products are worked up and isolated by generally customary methods (cf. also the Preparation Examples).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

Here, the active compounds according to the invention can be employed with particularly good success for combating dicotyledon weeds, in particular in monocotyledon crops, such as, for example, wheat or corn.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans. Mixtures with 2,4-dichlorophenoxyacetic acid (2,4-D); 2,4-dichlorophenoxypropionic acid (2,4-DP); 4-(2,4-dichlorophenoxy)butyric acid (2,4-DB); (2-methyl-4-chloro-phenoxy)-acetic acid (MCPA); (4-chloro-2-methyl-phenoxy)-propionic acid (MCPP); 3,5,6-trichloro-2-pyridyloxyacetic acid (TRICLOPYR); 2-[4-(2,4-dichlorophenoxy)-phenoxy]-propionic acid, its methyl ester or its ethyl ester (DICLOFOP); 2-chloro-4-ethylamino-6-isopropylamino-1,3,5-triazine (ATRAZINE); 3-isopropyl-2,1,3-benzothiadiazin-4-one 2,2-dioxide (BENTAZONE); methyl 5-(2,4-dichloro-phenoxy)-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-chloro-4-ethylamino-6-(3-cyanopropylamino)-1,3,5-triazine (CYANAZIN); 2-{4-[(6-chloro-2-benzoxazolyl)-oxy]-phenoxy}-propanoic acid, its methyl ester or its ethyl ester (FENOXAPROP); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); N-methyl-2-(1,3-benzothiazol-2-yloxy)-acetanilide (MEFENACET); 2-{[[((4-methoxy-6-methyl-1,3,5-triazin-2-yl)-amino)-carbonyl]amino]-sulphonyl}-benzoic acid or its methyl ester (METSULFURON); N-(1-ethyl-propyl)-3,4-dimethyl-2,6-dinitroaniline (PENDIMETHALIN); 0-(6-chloro-3-phenylpyridazin-4-yl) S-octyl thiocarbonate (PYRIDATE); 4-ethylamino-2-t-butylamino-6-methylthio-s-triazine (TERBUTRYNE); and methyl 3-[[[[(4-methoxy-6-methyl-1,3,5 -triazin-2-yl)-amino]-carbonyl]-amino]-sulphonyl]-thiophene-2-carboxylate (THIAMETURON) may also be advantageous. Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

Preparation Examples

EXAMPLE 1

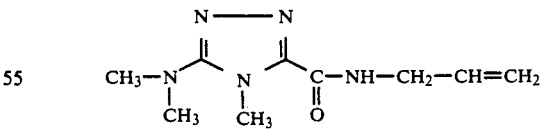

(Process a)

13.73 g (0.09 mole) of 1-amino-2,2,3-trimethyl-guanidinium hydrochloride, 14.13 g (0.09 mole) of monoethyl oxalate N-allylamide and 9.72 g (0.18 mole) of sodium methoxide are stirred for 30 minutes at 80° C. in 200 ml of ethanol, and the mixture is filtered and evaporated in vacuo. The residue is taken up in 200 ml of dichloromethane, and the mixture is washed with water, dried over sodium sulphate, evaporated in vacuo and recrystallized from ligroin/toluene (95:5).

4.07 g (22% of theory) of N-allyl-5-.dimethylamino-4-methyl-4H-1,2,4-triazol-3-yl-carboxamide of melting point 63° C.-65° C. are obtained.

EXAMPLE 2

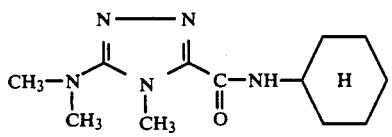

(Process a)

61 g (0.4 mole) of 1-amino-2,2,3-trimethylguanidinium hydrochloride, 79.6 g (0.4 mole) of monoethyl oxalate N-cyclohexylamide and 43.2 g (0.8 mole) of sodium methoxide are stirred for 1 hour at reflux temperature in 800 ml of ethanol, the mixture is cooled to room temperature, acidified with acetic acid and filtered, the filtrate is evaporated in vacuo, the residue is taken up in dichloromethane, and the mixture is washed three times with 150 ml portions of water, dried over sodium sulphate and evaporated in vacuo.

52.6 g (53% of theory) of N-cyclohexyl-5-dimethylamino-4-methyl-4H-1,2,4-triazol-3-yl-carboxamide of melting point 60° C.-62° C. are obtained.

Preparation of the Starting Compounds

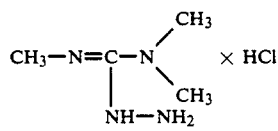

A solution of 78.5 g (0.5 mole) of chlorotrimethylformamidinium hydrochloride in 250 ml of isopropanol is added dropwise, with stirring, at 20° C. to 25° C. and in the course of 30 minutes to 50 g (1 mole) of hydrazine hydrate in 300 ml of isopropanol, when the addition is complete, the mixture is stirred for a further 30 minutes at room temperature, any hydrazine hydrochloride which has precipitated is filtered off with suction and washed with 150 ml of isopropanol, and the isopropanol filtrate is evaporated in vacuo.

70.7 g (93% of theory) of 1-amino-2,2,3-trimethylguanidinium hydrochloride, which is reacted further without purification, are obtained.

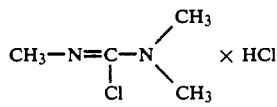

545 g (5.5 moles) of phosgene are passed at 80° C., with stirring and in the course of 2.5 hours into a mixture of 510 g (5 moles) of N,N,N'-trimethylurea and 3 liters of chlorobenzene; when all the phosgene has been passed in, the mixture is stirred for a further 45 minutes at 80° C. until carbon dioxide is no longer evolved. The reaction mixture is cooled to 10° C., and the product, which is sensitive to water, is filtered off with suction under nitrogen, washed with 1 liter of chlorobenzene and with two 500 ml portions of petroleum ether and dried in vacuo.

635.3 g (81% of theory) of chlorotrimethylformamidinium hydrochloride of melting point 76° C. to 78° C. are obtained.

EXAMPLE 3

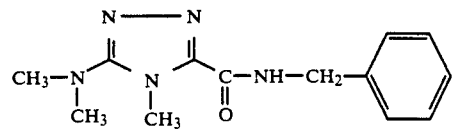

(Process b)

6 g (0.03 mole) of ethyl 5-dimethylamino-4-methyl-4H-1,2,4-triazol-3-yl-carboxylate and 4.28 g (0.04 mole) of benzylamine are heated in 80 ml of tetrahydrofuran at 200° C. at 20 bar. For working up, the mixture is evaporated in vacuo, and the residue is purified on silica gel by means of chromatography (eluent: toluene/ethanol 1:1). 2.68 g (35% of theory) of N-benzyl-5-dimethylamino-4-methyl-4H-1,2,4-triazol-3-yl-carboxamide of melting point 96° C.-98° C. are obtained.

Preparation of the Starting Compound

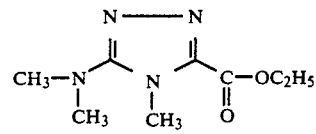

15.25 g (0.1 mole) of 1-amino-2,2,3-trimethylguanidinium hydrochloride and 14.6 g (0.1 mole) of diethyl oxalate are stirred in 100 ml of dichlorobenzene at 180° C. for 8 hours, the mixture is then evaporated in vacuo, and the product is chromatographed over silica gel (eluent: toluene/ethanol 1:1).

3.0 g (15% of theory) of ethyl 5-dimethylamino-4-methyl-4H-1,2,4-triazol-3-yl-carboxylate of melting point 52° C.-53° C. are obtained.

The following substituted triazoles of the general formula (i) are obtained in a corresponding manner and following the general instructions for the preparation:

TABLE 1

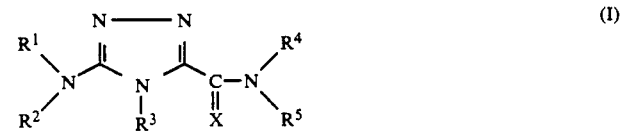

| Ex. No. | $R^1$ | $R^2$ | $R^3$ | $R^4$ | $R^5$ | X | Physical Properties |
|---|---|---|---|---|---|---|---|
| 4 | $CH_3$ | $CH_3$ | $CH_3$ | H | H | O | M.p. 173-174° C. |
| 5 | $CH_3$ | $CH_3$ | $CH_3$ | H |  | O | M.p. 103-105° C. |

TABLE 1-continued

Structure (I):
N═N, R¹R²N-C(=)-N(R³)-C(=X)-N(R⁴)(R⁵)

| Ex. No. | R¹ | R² | R³ | R⁴ | R⁵ | X | Physical Properties |
|---|---|---|---|---|---|---|---|
| 6 | CH₃ | CH₃ | CH₃ | H | —C(CH₃)(CH₃)—CF₃ | O | ¹H-NMR*: 1.7; 7.3 |
| 7 | CH₃ | CH₃ | CH₃ | H | —C(CH₂F)(CH₃)—CH₂F | O | ¹H-NMR*: 1.5; 4.6 |
| 8 | CH₃ | CH₃ | CH₃ | H | —C(CN)(CH₃)—C₂H₅ | O | M.p. 129–131° C. |
| 9 | CH₃ | CH₃ | CH₃ | H | —C(CH₃)₃ | O | M.p. 64–65° C. |
| 10 | CH₃ | CH₃ | CH₃ | H | —CH₂—C(CH₃)₃ | O | ¹H-NMR*: 0.9; 3.2 |
| 11 | CH₃ | CH₃ | CH₃ | H | —CH(CN)—C(CH₃)₃ | O | M.p. 106–108° C. |
| 12 | CH₃ | CH₃ | CH₃ | H | —C(CN)(CH₃)-cyclopropyl | O | M.p. 114–115° C. |
| 13 | CH₃ | CH₃ | CH₃ | H | —CH(CH₃)—C₆H₅ | O | M.p. 116–118° C. |
| 14 | CH₃ | CH₃ | CH₃ | CH₃ | —CH₂—CH₂—CN | O | M.p. 87–89° C. |
| 15 | CH₃ | CH₃ | CH₃ | H | 4-methylcyclohexyl (H, CH₃) | O | ¹H-NMR*: 1.0–2.0; 4.1 |
| 16 | CH₃ | CH₃ | CH₃ | H | —C(CH₃)(CH₃)—CH₂—C(CH₃)₃ | O | ¹H-NMR*: 1.0; 1.5; 1.8 |
| 17 | CH₃ | CH₃ | CH₃ | H | —(CH₂)₅—CH₃ | O | M.p. 30–32° C. |
| 18 | CH₃ | CH₃ | CH₃ | H | —CH(CH₃)—C₂H₅ | O | ¹H-NMR*: 0.9–1.0; 1.2–1.25; 1.5–1.6 |
| 19 | CH₃ | CH₃ | CH₃ | H | —CH(CH₃)₂ | O | ¹H-NMR*: 1.25; 4.1–4.2 |
| 20 | CH₃ | CH₃ | CH₃ | H | —CH₂—CH₂-(cyclohex-1-enyl) | O | ¹H-NMR*: 1.5–2.0; 2.3; 3.4; 5.5 |
| 21 | CH₃ | CH₃ | CH₃ | H | —CH(CH(CH₃)₂)(CH(CH₃)₂) | O | ¹H-NMR*: 0.9; 1.9; 3.6 |

TABLE 1-continued $$\begin{array}{c} R^1 \\ \diagdown \\ R^2 \end{array} N - C \begin{array}{c} N = N \\ \diagdown \\ N \\ | \\ R^3 \end{array} C = N \begin{array}{c} R^4 \\ \diagdown \\ R^5 \end{array} \quad (I)$$

| Ex. No. | $R^1$ | $R^2$ | $R^3$ | $R^4$ | $R^5$ | X | Physical Properties |
|---|---|---|---|---|---|---|---|
| 22 | CH₃ | CH₃ | CH₃ | H | —CH(CH₃)—(CH₂)₂—C₆H₅ | O | ¹H-NMR*: 1.3–1.9; 2.7; 4.2; 7.2 |
| 23 | CH₃ | CH₃ | CH₃ | H | —CH₂—C(CH₃)₂—CH₂—N(CH₃)₂ | O | ¹H-NMR*: 1.0; 2.3; 2.35; 3.3 |
| 24 | CH₃ | CH₃ | CH₃ | H | —(CH₂)₃—OC₂H₅ | O | ¹H-NMR*: 1.2; 1.8; 3.5 |
| 25 | CH₃ | CH₃ | CH₃ | H | —CH₂—CH₂—Cl | O | ¹H-NMR*: 3.6; 3.7 |
| 26 | CH₃ | CH₃ | CH₃ | H | —(CH₂)₃—CH₃ | O | M.p. 38–42° C. |
| 27 | CH₃ | CH₃ | CH₃ | H | 2-methylcyclohexyl | O | ¹H-NMR*: 0.9; 1.0–2.0 |
| 28 | CH₃ | CH₃ | CH₃ | H | 3-methylcyclohexyl | O | ¹H-NMR*: 0.9 |
| 29 | CH₃ | CH₃ | CH₃ | H | cyclopentyl | O | ¹H-NMR*: |
| 30 | CH₃ | CH₃ | CH₃ | H | —CH₂—CH(CH₃)₂ | O | M.p. 91–94° C. |
| 31 | CH₃ | CH₃ | CH₃ | H | —CH₂—CH₂—OC₂H₅ | O | M.p. 66–72° C. |
| 32 | CH₃ | CH₃ | CH₃ | H | —(CH₂)₂—CH₃ | O | M.p. 77–78° C. |
| 33 | CH₃ | CH₃ | CH₃ | H | 1-methylcyclopentyl | O | M.p. 72–73° C. |
| 34 | CH₃ | CH₃ | CH₃ | H | 1-ethylcyclohexyl | O | |
| 35 | CH₃ | H | CH₃ | H | 1-methylcyclohexyl | O | M.p. 238–239° C. |
| 36 | CH₃ | CH₃ | CH₃ | H | —CH(CH₃)—CH₂—OCH₃ | O | ¹H-NMR*: 1.3; 4.3; |
| 37 | CH₃ | CH₃ | CH₃ | H | —CH(CH₃)—CH₂Cl | O | ¹H-NMR*: 1.4; 4.4 |

TABLE 1-continued $$\underset{\underset{R^2}{\overset{R^1}{\diagdown}}}{N}-\underset{\underset{R^3}{\overset{|}{N}}}{C}-\underset{\underset{\overset{||}{X}}{\overset{|}{C}}}{\overset{N-N}{\diagdown}}\underset{R^5}{\overset{R^4}{\diagup}}\qquad (I)$$

| Ex. No. | R¹ | R² | R³ | R⁴ | R⁵ | X | Physical Properties |
|---|---|---|---|---|---|---|---|
| 38 | CH₃ | CH₃ | CH₃ | H | —CH₂—CH(C₂H₅)—(CH₂)₃—CH₃ | O | ¹H-NMR*: 3.3–3.4 |
| 39 | CH₃ | CH₃ | CH₃ | H | —C(CH₃)(CH₃)—C₂H₅ | O | ¹H-NMR*: 1.4; |
| 40 | CH₃ | CH₃ | CH₃ | H | —CH(CH₃)—CH₂—CH(CH₃)₂ | O | ¹H-NMR*: 4.15 |
| 41 | CH₃ | CH₃ | CH₃ | H | —(CH₂)₄—C₆H₅ | O | ¹H-NMR*: 7.1–7.3 |
| 42 | CH₃ | CH₃ | CH₃ | H | —CH(CH₃)—(CH₂)₄—CH₃ | O | ¹H-NMR*: 4.1 |
| 43 | CH₃ | CH₃ | CH₃ | H | —CH(CH₃)—CH(CH₃)₂ | O | ¹H-NMR*: 1.2; 1.7–1.8 |
| 44 | CH₃ | CH₃ | CH₃ | H | —CH(CH₃)—(CH₂)₃—CH(CH₃)₂ | O | ¹H-NMR*: 2.1; 4.1 |
| 45 | CH₃ | CH₃ | CH₃ | H | —C(CH₃)(CH₃)—C≡CH | O | ¹H-NMR*: 1.75 |
| 46 | CH₃ | CH₃ | CH₃ | H | —CH₂—CH(CH₃)—C₂H₅ | O | mp. 40–42° C. |
| 47 | CH₃ | CH₃ | CH₃ | H | —CH(CH₃)—CH₂—CH₂—CH₃ | O | ¹H-NMR*: 4.1 |
| 48 | CH₃ | CH₃ | CH₃ | H | —CH(C₂H₅)—(CH₂)₃—CH₃ | O | ¹H-NMR*: 3.95 |
| 49 | CH₃ | CH₃ | C₂H₅ | H | —CH(CH₃)—C₂H₅ | O | ¹H-NMR*: 4.25–4.35 |
| 50 | CH₃ | CH₃ | CH₃ | H | —CH(C₂H₅)(C₂H₅) | O | ¹H-NMR*: 0.95 |
| 51 | CH₃ | CH₃ | C₂H₅ | H | —CH(CH₃)—C₆H₅ | O | mp. 121–123° C. |
| 52 | CH₃ | CH₃ | C₂H₅ | H | —C(CH₂F)(CH₃)(CH₂F) | O | ¹H-NMR*: 1.35–1.40 |
| 53 | CH₃ | CH₃ | C₂H₅ | H | —CH(CH₃)₂ | O | ¹H-NMR*: |

TABLE 1-continued $$\begin{array}{c} \text{N}\text{---}\text{N} \\ R^1\diagdown\phantom{xx}\diagup\phantom{x}\diagdown R^4 \\ \phantom{xx}\text{N}\phantom{xxx}\text{N}\phantom{x}\diagup \\ R^2\diagup\phantom{x}|\phantom{x}\diagdown\phantom{x}\text{C}\text{---}\text{N} \\ \phantom{xxxxx}R^3\phantom{x}||\phantom{x}\diagdown R^5 \\ \phantom{xxxxxxxx}\text{X} \end{array}$$ (I)

| Ex. No. | $R^1$ | $R^2$ | $R^3$ | $R^4$ | $R^5$ | X | Physical Properties |
|---|---|---|---|---|---|---|---|
| 54 | $CH_3$ | $CH_3$ | $CH_3$ | H | $-\underset{\underset{CH_3}{\mid}}{\overset{\overset{CH_3}{\mid}}{C}}-CH(CH_3)_2$ | O | 1,4–1,45 $^1$H-NMR*: 0.9–0.95 |
| 55 | $CH_3$ | $CH_3$ | $CH_3$ | H | $CH_3$ | O | M.p. 95–98° C. |
| 56 | $CH_3$ | $CH_3$ | $CH_3$ | H | $-CH_2-\text{(3-pyridyl)}$ | O | M.p. 117–118° C. |
| 57 | $CH_3$ | $CH_3$ | $CH_3$ | H | $\underset{Cl}{\overset{CH_3}{\diagdown}}\text{C}\underset{F}{\overset{F}{\diagup}}\text{CF}$ | O | M.p. 155–157° C. |
| 58 | $CH_3$ | $CH_3$ | $CH_3$ | H | cyclobutyl | O | |
| 59 | $CH_3$ | $CH_3$ | $CH_3$ | $C_2H_5$ | $C_2H_5$ | O | |
| 60 | $CH_3$ | $CH_3$ | $CH_3$ | H | $-\underset{\underset{CH_3}{\mid}}{\overset{\overset{CH_3}{\mid}}{C}}-CH_2F$ | O | |
| 61 | $CH_3$ | $CH_3$ | $CH_3$ | $-CH(CH_3)_2$ | $-CH(CH_3)_2$ | O | |
| 62 | $C_2H_5$ | $C_2H_5$ | $CH_3$ | H | $-\underset{\underset{CH_3}{\mid}}{CH}-C_2H_5$ | O | M.p. 57–59° C. |

*The $^1$H-NMR spectra were recorded in deuterochloroform (CDCl$_3$) with tetramethylsilane (TMS) as the internal standard. The chemical shift is indicated as δ value in ppm.

USE EXAMPLES

In the following use examples, the compound indicated below was employed as comparison substance:

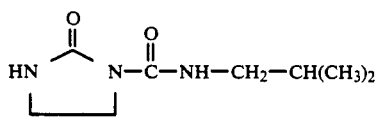
(A)

N-Isobutylimidazolidin-2-one-1-carboxamide (known from K.H. Büchel, "Pflanzenschutz und Schädlingsbekämpfung" [Plant Protection and Pest Control] p. 170, Thieme Verlag Stuttgart 1977)

EXAMPLE A

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity compared with comparison substance (A) is shown by, for example, the compounds according to the following Preparation Examples: 2, 6, 9, 10, 11, 18 and 19.

EXAMPLE B

Post-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in damage in comparison to the development of the untreated control. The figures denote:

0% = no action (like untreated control)
100% = total destruction

In this test, a clearly superior activity compared with comparison substance (A) combined with a comparably good selectivity towards crop plants is shown by, for example, the compounds according to the following Preparation Examples: 2, 7, 10, 11, 13, 14, 15, 18, 19, 22 and 25.

It will be appreciated that the instant specification and claims are set forth by way of illustration and not limitation, and that various modifications and changes may be made without departing from the spirit and scope of the present invention.

We claim:
1. A substituted triazole of the formula

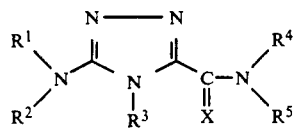

in which
$R^1$ and $R^2$ independently of one another each stands for hydrogen, for in each case straight-chain or branched alkyl which has 1 to 8 carbon atoms, alkenyl which as 2 to 8 carbon alkynyl which has 2 to 8 carbon atoms, halogenoalkyl which has 1 to 8 carbon atoms and 1 and 17 identical or different halogen atoms, halogenoalkenyl which has 2 to 8 carbon atoms and 1 to 15 identical or different halogen atoms, halogenoalkynyl which has 2 to 8 carbon atoms and 1 to 13 identical or different halogen atoms, alkoxyalkyl which has 1 to 6 carbon atoms in the individual alkyl moieties, for cycloalkyl which has 3 to 7 carbon atoms, for cycloalkylalkyl which has 3 to 7 carbon atoms in the cycloalkyl moiety and 1 to 6 carbon atoms in the straight-chain or branched alkyl moiety or for aralkyl which has 6 to 10 carbon atoms in the aryl moiety and 1 to 6 carbon atoms in the straight-chain or branched alkyl moiety, aryl which has 6 to 10 carbon atoms and which is optionally substituted once or more than once by identical or different substituents from the group consisting of halogen, cyano, nitro, in each case straight-chain or branched alkyl, alkoxy or alkylthio, and in each case straight-chain or branched halogenoalkyl, halogenoalkoxy or halogenoalkylthio, each of which has 1 to 4 carbon atoms and 1 to 9 identical or different halogen atoms, $R^3$ stands for in each case straight-chain or branched alkyl which has 1 to 8 carbon atoms, alkenyl which has 2 to 8 carbon atoms, alkynyl which has 2 to 8 carbon atoms, halogenoalkyl which has 1 to 8 carbon atoms and 1 to 17 identical or different halogen atoms, halogenoalkenyl which has 2 to 8 carbon atoms and 1 to 15 identical or different halogen atoms, halogenoalkynyl which has 2 to 8 carbon atoms and 1 to 13 identical or different halogen atoms, alkoxyalkyl which has 1 to 6 carbon atoms in each of the individual alkyl moieties, for cycloalkylalkyl which has 3 to 7 carbon atoms in the cycloalkyl moiety and 1 to 6 carbon atoms in the straight-chain or branched alkyl moiety, for cycloalkyl which has 3 to 7 carbon atoms, or for aralkyl which has 6 to 10 carbon atoms in the aryl moiety and 1 to 6 carbon atoms in the straight-chain or branched alkyl moiety, or aryl which has 6 to 10 carbon atoms, the aralkyl or aryl being optionally substituted once or more than once by identical or different substituents selected from the group consisting of halogen, cyano, nitro and in each case straight-chain or branched alkyl, alkoxy or alkylthio having 1 to 4 carbon atoms, or halogenoalkyl, halogenoalkoxy or halogenoalkylthio, each of which has 1 to 4 carbon atoms and 1 to 9 identical or different halogen atoms, $R^4$ and $R^5$ independently of one another each stands for hydrogen, for in each case straight-chain or branched alkyl which has 1 to 18 carbon atoms, alkenyl which has 2 to 8 carbon atoms, alkynyl which has 2 to 8 carbon atoms, halogenoalkyl which has 1 to 8 carbon atoms and 1 to 17 identical or different halogen atoms, halogenoalkenyl which has 2 to 8 carbon atoms and 1 to 15 identical or different halogen atoms, halogenoalkynyl which has 2 to 8 carbon atoms and 1 to 13 identical or different halogen atoms, cyanoalkyl which has 1 to 8 carbon atoms, hydroxyalkyl which has 1 to 8 carbon atoms and 1 to 6 hydroxyl groups, alkoxyalkyl, alkoximinoalkyl, alkoxycarbonylalkyl or alkoxycarbonylalkenyl each of which has up to 6 carbon atoms in the individual alkyl or alkenyl moieties, alkylaminoalkyl or dialkylaminoalkyl each of which has 1 to 6 carbon atoms in the individual alkyl moieties, or for cycloalkyl, cycloalkylalkyl, cycloalkenyl or cycloalkenylalkyl each of which has 3 to 8 carbon atoms in the cycloalkyl or cycloalkenyl moiety, and if appropriate 1 to 6 carbon atoms in the straight-chain or branched alkyl moiety when present and each of which is optionally substituted once or more than once by identical or different substituents from the group consisting of halogen, cyano and in each case straight-chain or branched alkyl which has 1 to 9 carbon atoms or halogenoalkyl which has 1 to 4 carbon atoms and 1 to 9 identical or different halogen atoms or in each case double-linked alkanediyl or alkenediyl each of which has up to 4 carbon atoms; in addition, for aralkyl, aroyl or aryl each of which has 6 to 10 carbon atoms in the aryl moiety and if appropriate 1 to 8 carbon atoms in the straight-chain or branched alkyl moiety and each of which is optionally substituted once or more than once by identical or different substituents selected from the group consisting of halogen, cyano, nitro, hydroxyl, in each case straight-chain or branched alkyl, alkoxy, alkylthio, alkylsulphinyl, alkylsulphonyl, alkanoyl or alkoxycarbonyl each of which has 1 to 6 carbon atoms, and halogenoalkyl, halogenoalkoxy, halogenoalkylthio, halogenoalkylsulphinyl or halogenalkylsulphonyl each of which has 1 to 6 carbon atoms and 1 to 9 identical or different halogen atoms, cycloalkyl which has 3 to 6 carbon atoms or phenoxy, and the alkyl radicals optionally being substituted by halogen or cyano, and X stands for oxygen or sulphur.

2. A substituted triazole according to claim 1, in which $R^1$ and $R^2$ independently of one another each stands for hydrogen, for methyl, ethyl, n- or i-propyl, n-, i-, s- or t-butyl, n- or i-pentyl, allyl, propargyl, for in each case straight-chain or branched halogenoalkyl which has 1 to 4 carbon atoms, halogenoalkenyl which has 3 to 6 carbon atoms or halogenoalkynyl which has 3 to 6 carbon atoms, each of which has 1 to 9 identical or different halogen atoms, for methoxymethyl, methoxyethyl, for cyclopropyl, cyclopropylmethyl, cyclopentyl, cyclohexyl, cyclohexylmethyl, cyclohexylethyl, cyclopentylmethyl or for benzyl, phenylethyl or phenyl, each of which is optionally substituted once to three times by identical or different substituents selected from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio, $R^3$ stands for methyl, ethyl, n- or i-propyl, n-, i-, s- or t-butyl, n- or i-pentyl, n- or i-hexyl, for allyl, propargyl, for methoxymethyl, for straight-chain or branched halogenoalkyl which has 1 to 4 carbon atoms and 1 to 9 identical or different halogen atoms, for cyclopentyl, cyclohexyl, cyclopropyl, cyclopropylmethyl, cyclohexylmethyl, cyclohexylethyl or for benzyl or phenyl, each of which is optionally substituted once to three times by identical or different substituents selected from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio, $R^4$ and $R^5$ independently of one another each stands for hydrogen, methyl, ethyl, n- or i-propyl, n-, i-, s- or t-butyl, in each case straight-chain or branched pentyl, hexyl, heptyl, octyl, nonyl, decyl, or dodecyl, for allyl, n- or i-butenyl, n- or i-pentenyl, n- or i-hexenyl, propargyl, n- or i-butynyl, or n- or i-pentynyl, n- or i-hexynyl, for straight-chain or branched halogenoalkyl which has 1 to 6 carbon atoms and 1 to 9 identical or different halogen atoms, for in each case straight-chain or branched halogenoalkenyl or halogenoalkynyl each of which has 3 to 5 carbon atoms and 1 to 3 halogen atoms, for in each case straight-chain or branched cyanoalkyl which has 1 to 6 carbon atoms in the alkyl moiety, hydroxyalkyl which has 1 to 6 carbon atoms and 1 to 3 hydroxyl groups, alkoxyalkyl, alkoximinoalkyl, alkoxycarbonylalkyl, alkoxycarbonyl-alkenyl, alkylaminoalkyl or dialkylaminoalkyl, each of which has up to 4 carbon atoms in the individual alkyl or alkenyl moieties, or for cyclopropyl, cyclopropylmethyl, cyclopropylethyl, cyclobutyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is optionally substituted once to three times by identical or different substituents selected from the group consisting of fluorine, chlorine, bromine, methyl, ethyl, n- or i-propyl, n-, i-, s- or t-butyl, cyano, methanediyl, ethanediyl, butanediyl and butadienediyl; additionally stands for optionally straight-chain or branched benzyl, phenylethyl, phenylpropyl, phenylbutyl, phenylpentyl, phenylhexyl, phenylheptyl, phenylcyanomethyl, phenylcyanoethyl, phenylcyanopropyl, benzoyl, phenyl or naphthyl, each of which is optionally ring substituted once to three times by identical or different substituents selected from the group consisting of fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl and phenoxy, and X stands for oxygen or sulphur.

3. A substituted triazole according to claim 1, in which $R^1$ stands for hydrogen, methyl or ethyl, $R^2$ stands for methyl or ethyl, $R^3$ stands for methyl or ethyl, $R^4$ stands for hydrogen or methyl, $R^5$ stands for hydrogen, methyl, ethyl, n- or i-propyl, n-, i-, s- or t-butyl, in each case straight-chain or branched pentyl, hexyl, heptyl, octyl, nonyl, decyl or dodecyl, for allyl, n- or i-butenyl, n- or i-pentenyl, n- or i-hexenyl, propargyl, n- or i-butynyl, n- or i-pentynyl, n- or i-hexynyl, for straight-chain or branched halogenoalkyl which has 1 to 6 carbon atoms and 1 to 9 identical or different halogen atoms, for in each case straight-chain or branched halogenoalkenyl or halogenoalkynyl each of which has 3 to 5 carbon atoms and 1 to 3 halogen atoms, for in each case straight-chain or branched cyanoalkyl which has 1 to 6 carbon atoms in the alkyl moiety, hydroxyalkyl which has 1 to 6 carbon atoms and 1 to 3 hydroxyl groups, alkoxyalkyl, alkoximinoalkyl, alkoxycarbonylalkyl or alkoxycarbonylalkenyl, alkylaminoalkyl or dialkylaminoalkyl, each of which has up to 4 carbon atoms in the individual alkyl or alkenyl moieties, or for cyclopropyl, cyclopropylmethyl, cyclopropylethyl, cyclobutyl, cyclopentyl, cyclohexyl, cycloheptyl, cyclooctyl, cyclohexylmethyl, cyclohexylethyl, cyclohexenyl, cyclohexenylmethyl or cyclohexenylethyl, each of which is optionally substituted once to three times by identical or different substituents from the group consisting of fluorine, chlorine, bromine, methyl, ethyl, n- or i-propyl, n-, i-, s- or t-butyl, cyano, methanediyl, ethanediyl, butanediyl and butadienediyl; additionally stands for in each case straight-chain or branched benzyl, phenylethyl, phenylpropyl, phenylbutyl, phenylpentyl, phenylhexyl, phenylheptyl, phenylcyanomethyl, phenylcyanoethyl, phenylcyanopropyl, benzoyl, phenyl or naphthyl, each of which is optionally substituted once to three times in the phenyl moiety by identical or different substituents from the group consisting of fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl and phenoxy, and X stands for oxygen.

4. A substituted triazole according to claim 1, in which $R^1$ stands for methyl or ethyl, $R^2$ stands for methyl or ethyl, $R^3$ stands for methyl or ethyl, R[4] stands for hydrogen or methyl, R[5] stands for hydrogen, methyl, ethyl, n- or i-propyl, n-, i-, s- or t-butyl, n- or isopentyl, hexyl, heptyl, octyl, nonyl, decyl or dodecyl, for allyl, n- or i-butenyl, n- or i-pentenyl, n- or i-hexenyl, propargyl, n- or i-butynyl, n- or i-pentynyl, n- or i-hexynyl, for straight-chain or branched halogenoalkyl which has 1 to 6 carbon atoms and 1 to 9 identical or different halogen atoms, for in each case straight-chain or branched halogenoalkenyl or halogenoalkynyl, each of which has 3 to 5 carbon atoms and 1 to 3 halogen atoms for in each case straight-chain or branched cycloalkyl which as 1 to 6 carbon atoms in the alkyl moiety, hydroxyalkyl which has 1 to 6 carbon atoms and 1 to 3 hydroxyl groups or alkoxyalkyl which has 1 to 4 carbon atoms in the individual alkyl parts, or for cyclopropyl, cyclopropylmethyl, cyclopropylethyl, cyclobutyl, cyclopentyl, cyclohexyl, cycloheptyl, cyclooctyl, cyclohexylmethyl, cyclohexylethyl, cyclohexenyl, cyclohexenylmethyl or cyclohexenylethyl each of which is optionally substituted once to three times by identical or different substituents from the group consisting of fluorine, chlorine, bromine, methyl, ethyl, n- or i-propyl, n-, i-, s- or t-butyl and cyano; additionally stands for in each case straight-chain or branched benzyl, phenylethyl, phenylpropyl, phenylbutyl, phenylpentyl, phenylhexyl, phenylheptyl each of which is optionally substituted once to three times in the phenyl moiety by identical or different substituents from the group consisting of fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl and ethoxycarbonyl, and X stands for oxygen.

5. A compound according to claim 1, wherein such compound is N-(1-methyl-propyl)-5-dimethylamino-4-methyl-4H-1,2,4-triazol-3-yl-carboxamide of the formula

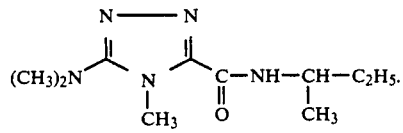

6. A compound according to claim 1, wherein such compound is N-isopropyl-5-dimethylamino-4-methyl-4H-1,2,4-triazol-3-yl-carboxamide of the formula

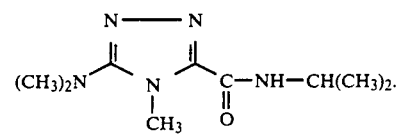

7. A herbicidal composition comprising a herbicidally effective amount of a compound according to claim 1 and a diluent.

8. A method of combatting unwanted vegetation which comprises applying to such vegetation or to a locus from which it is desired to exclude such vegetation a herbicidally effective amount of a compound according to claim 1.

9. The method according to claim 8, wherein such compound is
N-(1-methyl-propyl)-5-dimethylamino-4-methyl-4H-1,2,4-triazol-3-yl-carboxamide, or
N-isopropyl-5-dimethylamino-4-methyl-4H-1,2,4-triazol-3yl-carboxamide.

* * * * *

UNITED STATES PATENT AND TRADEMARK OFFICE
CERTIFICATE OF CORRECTION

PATENT NO. : 5,021,081

DATED : June 4, 1991

INVENTOR(S) : Findeisen et al.

It is certified that error appears in the above-identified patent and that said Letters Patent is hereby corrected as shown below:

On the title page, ABSTRACT: Line 23 after 1st " each " delete " each "

Col. 27, line 41  After 1st " carbon " insert -- atoms, --

Signed and Sealed this

Sixth Day of April, 1993

*Attest:*

STEPHEN G. KUNIN

*Attesting Officer*   Acting Commissioner of Patents and Trademarks